United States Patent
Goza et al.

(10) Patent No.: US 10,830,418 B2
(45) Date of Patent: Nov. 10, 2020

(54) HOUSING ASSEMBLY FOR LIGHT SOURCE

(71) Applicant: Proximity Systems, Inc., Houston, TX (US)

(72) Inventors: Jeremy Goza, Houston, TX (US); Jonathan Goza, Houston, TX (US); Michael Murphy, Scottsdale, AZ (US)

(*) Notice: Subject to any disclaimer, the term of this patent is extended or adjusted under 35 U.S.C. 154(b) by 0 days.

(21) Appl. No.: 16/263,862

(22) Filed: Jan. 31, 2019

(65) Prior Publication Data
US 2020/0200366 A1    Jun. 25, 2020

Related U.S. Application Data

(63) Continuation-in-part of application No. 29/674,332, filed on Dec. 20, 2018.

(51) Int. Cl.
| | | |
|---|---|---|
| *F21V 15/01* | (2006.01) | |
| *F21V 21/30* | (2006.01) | |
| *A61L 2/10* | (2006.01) | |
| *F21V 11/18* | (2006.01) | |
| *A61L 2/26* | (2006.01) | |
| *F21Y 103/00* | (2016.01) | |

(52) U.S. Cl.
CPC ............ *F21V 15/01* (2013.01); *A61L 2/10* (2013.01); *A61L 2/26* (2013.01); *F21V 11/183* (2013.01); *F21V 21/30* (2013.01); *A61L 2202/11* (2013.01); *F21Y 2103/00* (2013.01)

(58) Field of Classification Search
CPC .......... A61L 2/10; A61L 2/26; A61L 2202/11; F21V 15/10; F21V 11/183; F21V 21/30; F21V 2103/00; F21V 11/18; F21V 21/14; F21V 21/26; F21S 8/036; F21S 8/043
See application file for complete search history.

(56) References Cited

U.S. PATENT DOCUMENTS

| | | | |
|---|---|---|---|
| D133,214 S | 7/1941 | Ohm | |
| 4,779,178 A * | 10/1988 | Spitz | F21S 8/06 362/220 |
| 5,174,646 A * | 12/1992 | Siminovitch | F21V 19/0095 313/44 |
| 6,402,352 B1 * | 6/2002 | Summerford | F21S 8/088 362/269 |
| 6,644,829 B1 * | 11/2003 | Tracy | F21V 21/088 362/220 |
| D500,884 S | 1/2005 | O'Rourke | |
| 7,229,185 B1 * | 6/2007 | Galvez | F21L 14/023 362/109 |
| 8,142,047 B2 * | 3/2012 | Acampora | F21V 3/00 362/217.01 |
| D671,254 S | 11/2012 | Miyatake | |
| D686,772 S | 7/2013 | Waltz et al. | |
| D694,448 S | 11/2013 | Li | |
| 8,581,522 B2 | 11/2013 | Inskeep | |
| D712,104 S | 8/2014 | Stickney et al. | |
| 9,901,652 B2 | 2/2018 | Cole et al. | |

(Continued)

*Primary Examiner* — David E Smith
(74) *Attorney, Agent, or Firm* — Bushman Werner, P.C.

(57) ABSTRACT

A housing assembly for an illumination source such as a UV light where there is an enclosure formed by first and second releasably mateable housing shells and a bracket having a web, and first and second laterally extending flanges, the bracket being releasably connectable to said enclosure via the flanges, the enclosure having limited rotation relative to said bracket.

11 Claims, 3 Drawing Sheets

(56) References Cited

U.S. PATENT DOCUMENTS

| | | | |
|---|---|---|---|
| 2002/0044456 A1* | 4/2002 | Balestriero | F21V 29/87 |
| | | | 362/555 |
| 2007/0171653 A1* | 7/2007 | Bingaman | F21V 17/18 |
| | | | 362/346 |
| 2007/0171659 A1* | 7/2007 | Tickner | F21V 21/30 |
| | | | 362/371 |
| 2007/0297167 A1* | 12/2007 | Greenhoe | F21S 9/032 |
| | | | 362/183 |
| 2010/0296287 A1* | 11/2010 | Huang | F21V 15/013 |
| | | | 362/249.02 |
| 2013/0062534 A1 | 3/2013 | Cole | |
| 2015/0090903 A1 | 4/2015 | Cole | |
| 2015/0090904 A1 | 4/2015 | Cole | |
| 2017/0299161 A1* | 10/2017 | Boorom | F21V 29/508 |

* cited by examiner

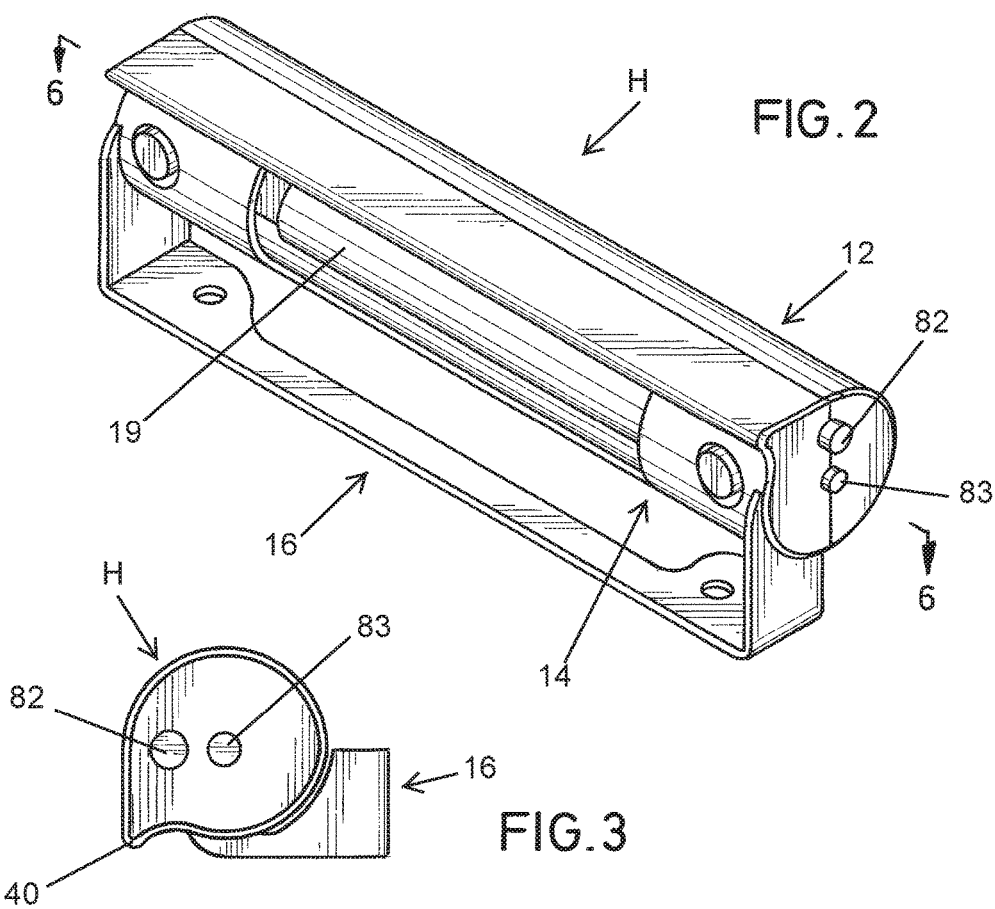
FIG. 2
FIG. 3
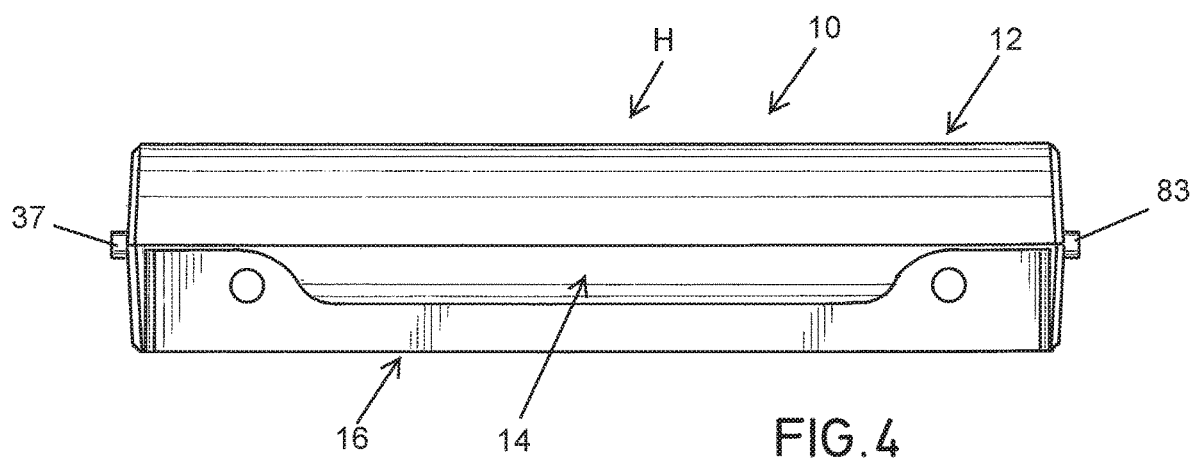
FIG. 4

HOUSING ASSEMBLY FOR LIGHT SOURCE

CROSS REFERENCE TO RELATED APPLICATION

This application is a continuation-in-part of U.S. application Ser. No. 29/674,322 filed on Dec. 20, 2018, the disclosure of which is incorporated herein by reference for all purposes.

FIELD OF THE INVENTION

The present invention relates to a housing assembly for a light source and, more particularly, to a housing assembly for a ultraviolet (UV) light.

BACKGROUND OF THE INVENTION

The prior art abounds with numerous housing assemblies which can be used with various types of light sources for various illumination purposes. In particular, UV disinfecting is widely used in hospitals, healthcare facilities, doctor's offices, and similar environments where germs can easily spread by virtue of human interaction with patients, instruments, surfaces, and the like. There are many, commercially available UV disinfectant systems which can be installed in hospitals or similar facilities where curtailment of the spread of germs is paramount.

U.S. Pat. No. 9,901,652 ('652 Patent), which is incorporated herein by reference for all purposes, discloses a UV disinfection apparatus that can be used in a hospital or similar facility.

SUMMARY OF THE INVENTION

In one aspect, the present invention relates to a housing for a light source.

In a further aspect, the present invention relates to a housing for a UV light source.

In yet a further aspect, the present invention relates to a housing for a UV light source which can be easily mounted in a variety of ways to focus disinfecting UV light on surfaces, instruments, tools, or the like which are periodically subject to human interaction.

These and further features and advantages of the present invention will become apparent from the following detailed description, wherein reference is made to the figures in the accompanying drawings.

BRIEF DESCRIPTION OF THE DRAWINGS

FIG. 2 is a perspective view showing the underside of the housing of FIG. 1 in an assembled position.

FIG. 3 is an end view of the embodiment shown in FIG. 1.

FIG. 4 is a rear, elevational view of the embodiment shown in FIG. 1.

DETAILED DESCRIPTION OF PREFERRED EMBODIMENTS

Figure 1:
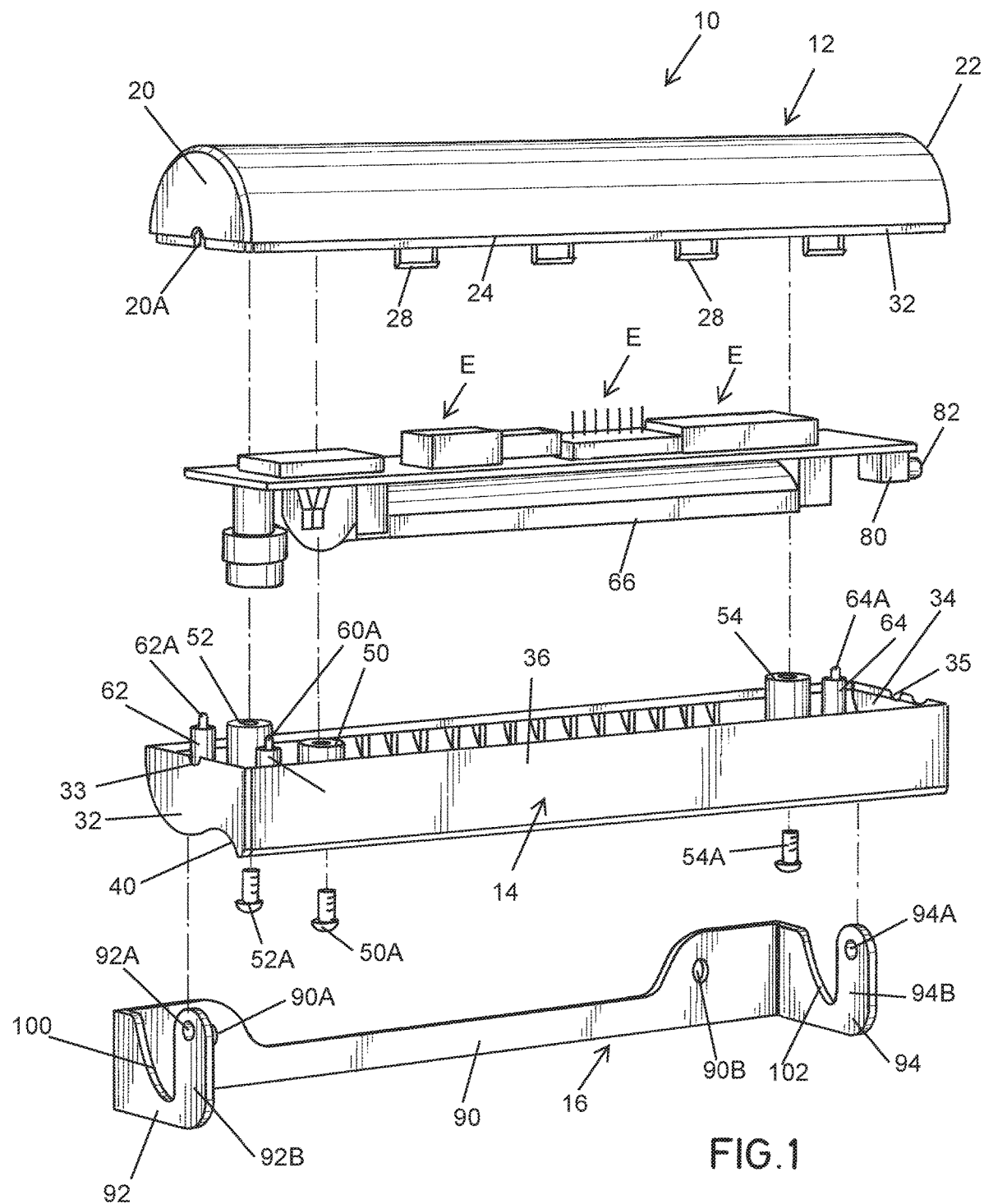
FIG. 1 is an exploded view of a housing assembly in accordance with one embodiment of the present invention.
Figure 5:
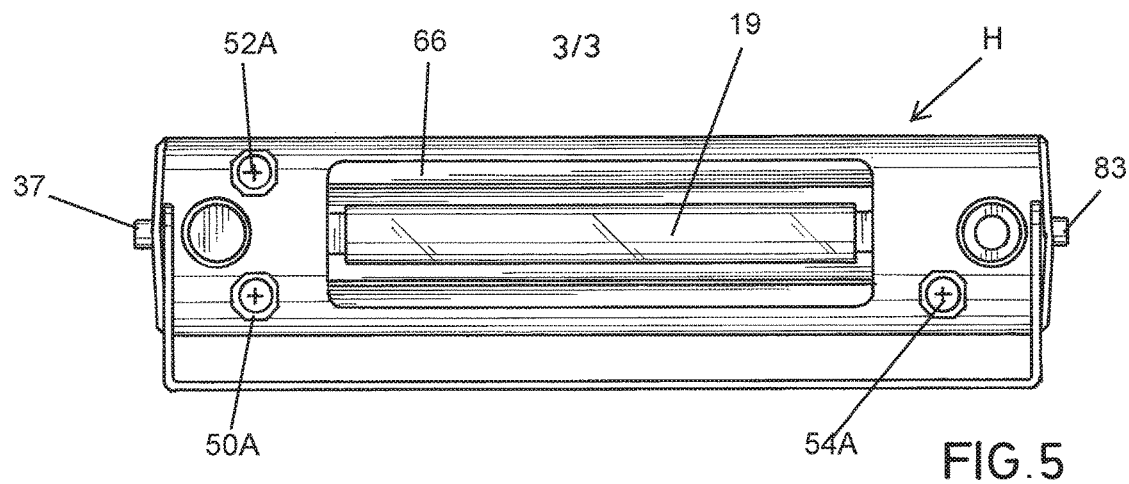
FIG. 5 is a bottom, plan view of the embodiment of FIG. 1, shown in an assembled position.

Referring first to FIG. 1, it can be seen that the housing assembly shown generally as 10 comprises first and second housing shells 12 and 14, a bracket 16 and an electronics board 18. As seen in FIG. 1, when connected, as described hereafter, shells 12 and 14 form an enclosure H which can have an electronics electronics board 18 on which are mounted various electronical components shown generally as E, the details of which are not germane to the present invention except to the extent they form sockets for a UV bulb 19, as best seen seen in FIGS. 5 and 6. When housing shells 12 and 14 are mated to form enclosure H, electronics board 18 is mounted therein as described hereafter.

Figures 7, 8, 9:
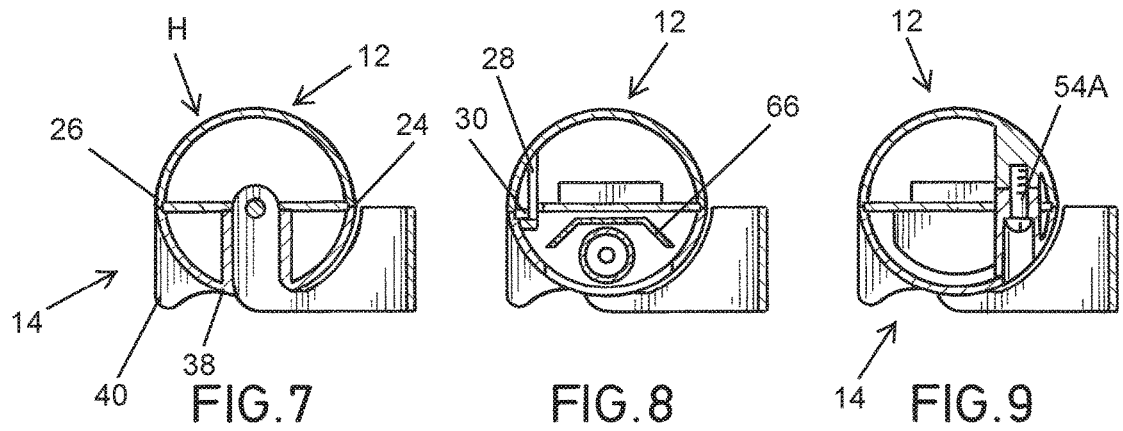
FIG. 7 is a cross-sectional view taken along the lines 7-7 of FIG. 6.
FIG. 8 is a cross-sectional view taken along the lines 8-8 of FIG. 6.
FIG. 9 is a cross-sectional view taken along the lines 9-9 of FIG. 6.

Housing shell 12, as best shown in any one of FIGS. 7-9, is generally semicircular in transverse cross-section and has a first end 20, a second end 22, a first side edge 24 and a second side edge 26 (see FIG. 7). Attached to the inner wall of housing shell 12 along first edge 24 are a plurality of spaced clips 28. As best seen in FIG. 8, when shells 12 and 14 are connected to form enclosure H, clips 28 snap over latch formations 30 formed on the inner wall of second housing shell 14. Further, housing shell 12 has a peripheral lip 32 which nests in second housing shell 14 when shells 12 and 14 are connected. Housing shell 14 has first end wall 32, a second end wall 34, and an elongate outer peripheral edge 36.

Figure 6:
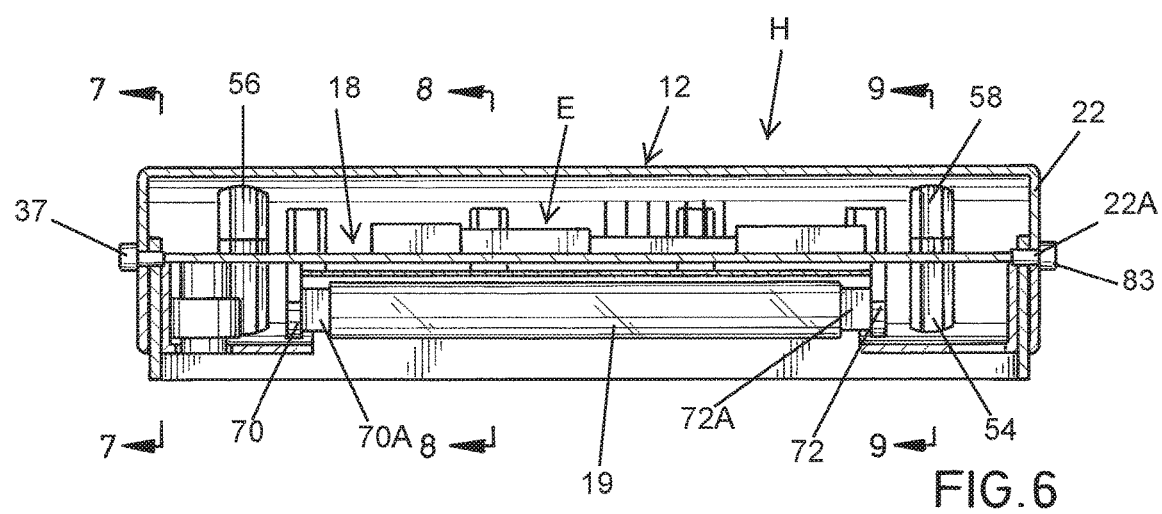
FIG. 6 is a cross-sectional view taken along the lines 6-6 of FIG. 2.

As can be seen from FIGS. 1 and 6, housing shell 12 has arcuate notches 20A and 22A in end walls 20 and 22, respectively. In like fashion there are arcuate notches 33 and 35 in end walls 32 and 34, respectively, of housing shell 14. As seen henceforth when shells 12 and 14 are brought together, notches 20A and 33 cooperate to form an aperture through one end wall of the enclosure H. Likewise, when the shells 12 and 14 are brought together, notches 22A and 35 form an aperture through the opposite end wall of the enclosure H.

As best shown in FIG. 1, housing shell 14 has an outer, generally undulating surface 38 forming a visor 40 which acts as a shield to keep UV light from emanating outwardly from the enclosure H and which also can be conveniently used as a gripping formation to rotate the enclosure H relative to the bracket 16 as described hereafter.

Housing shell 14 has three internal posts 50, 52, and 54, which have throughbores for receipt of screws 50A, 52A, and 54A, respectively. The screws 50A, 52A, and 54A extend through the electronics board 18 and threadedly engage three internally threaded corresponding posts, only two of which, 56 and 58, are shown (see FIG. 6), and which are formed in and extend from the interior wall of housing shell 12. There are also three alignment posts 60, 62, and 64 attached to the inner wall of housing shell 14, each of the alignment posts having tapered nubs 60A, 62A, and 64A which are received in holes (not shown) in electronics board 18, which help to align as well as hold the electronics board 18 and shell 14 in relative position to one another prior to final connection. Thus, it can be seen that electronics board 18 and its various components can be positioned in and securely mounted in the enclosure H when the housing shells 12 and 14 are assembled.

As noted, with respect to electronics board 18, and as can be seen in FIGS. 1 and 6, there are a plurality of electronic components E used for various purposes, not germane to the housing assembly 10 of the present invention. However, with respect to FIG. 6, it can be seen that electronics board 18 carries axially spaced socket mounts 70 and 72 on which are mounted sockets 70A and 72A, respectively, by which elongate UV bulb 19 can be removably mounted. There is a parabolic reflector 66 attached to electronics board 18 which helps direct UV light emanating from bulb 19 downwardly through an elongate opening 19A towards surfaces (not shown) to be subjected to UV sterilization. Attached to electronics board 18 is a switch 80 from which laterally extends an on/off button 82 extending externally of enclosure H (not shown).

To assemble the enclosure H together with the electronics board 18, electronics board 18 is mounted on shell 14 via engagement of nubs 60A, 62A, and 64A with corresponding sockets (not shown) in electronics board 18. Shells 12 and 14 are then brought together such that peripheral flange 32 nests inside housing shell 14. The nubs 60A-64A ensure proper alignment of the posts 50, 52, and 54 with corresponding threaded bores in electronics board 18 whereby screws 50A, 52A, and 54A can be threaded into the respective threaded bores in the internally threaded posts 56 and 58, and a third post not shown.

Lastly, to complete the housing assembly, bracket 16 is attached. In this regard, it can be seen that bracket 16 comprises a web 90 from opposite ends of which laterally outwardly extend flanges 92 and 94. Flanges 92 and 94 are provided with throughbores 92A and 94A, respectively, while web 90 is provided with throughbores 90A and 90B. As best seen in FIG. 6, housing shell 14 has slots at opposite ends through which arm portions 92B of flange 92 and 94B of flange 94 can extend until throughbores 92A and 94A are in register with the apertures in the opposite ends of the enclosure H formed by notches 20A/33 and 22A/35 formed in the end walls of the housing shells 12 and 14.

When thusly positioned, as to the apertures formed by notches 20A/33 and 22A/35, first and second rivets 84 and 37 can be used, the rivets serving to frictionally hold arms 92B and 94B in engagement with the enclosure H. As power button 82 protrudes from enclosure H as shown in FIG. 3.

It should be noted that flange 92 has a deep V-notch 100 and flange 94 has a deep V-notch 102. The notches 100 and 102 allow limited relative rotation between bracket 16 and the enclosure H. Thus, and by example only, if bracket 16 is affixed to a wall surface via throughbores 90A and 90B the enclosure H can be rotated, the rotation being limited by the inter-engagement between the notches 100 and 102 and the housing shell 14. It will be understood that bracket 16 can also be attached to a free standing stand if desired.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A housing assembly for an illumination source, comprising:
    an enclosure, comprising:
        a first elongate housing shell having a first end and a second end;
        a second elongate housing shell having a first end and a second end, said second housing shell having an elongate opening between said first and second ends of said second housing shell, said first and second housing shells being mateable to form an enclosure having a first enclosure end, a second enclosure end, a first aperture in said first enclosure end, and a second aperture in said second enclosure end;
    a bracket comprising:
        an elongate web portion having first and second web ends;
        a first flange extending from said first web end;
        a second flange extending from said second web end, each of said first and second flanges having first and second throughbores, respectively, said first flange extending into said enclosure adjacent said first enclosure end, said second flange extending into said enclosure adjacent said second enclosure end, said first throughbore being in register with said first aperture to form a first pivot passage, said second throughbore being in register with said second aperture to form a second pivot passage;
    a first pivot received in said first fastening passage; and
    a second pivot received in said second fastening passage.

2. The housing assembly of claim 1, wherein said enclosure is rotatable relative to said bracket around said first and second pivots.

3. The housing assembly of claim 1, wherein said first pivot comprise a rivet.

4. The housing assembly of claim 1, wherein said second pivot comprises a rivet.

5. The housing assembly of claim 1, wherein said first housing shell is generally semi-circular when viewed in transverse cross-section.

6. The housing assembly of claim 1, wherein said second shell has an undulating, outer surface.

7. The housing assembly of claim 6, wherein said undulating, outer surface forms a visor.

8. The housing assembly of claim 1, wherein said second shell has an elongate opening between said first end and said second end.

9. The housing assembly of claim 1, wherein said first shell has a peripheral lip, said lip being received in said second shell when said first and second shells are connected to form said enclosure.

10. The housing assembly of claim 1, wherein there is a mount for an elongate light bulb positioned in said enclosure.

11. The housing assembly of claim 10, wherein said elongate light bulb comprises a UV bulb.

* * * * *